United States Patent [19]

Olesen

[11] 4,406,302

[45] Sep. 27, 1983

[54] POP-OFF GAS EVACUATOR VALVE FOR ANESTHESIA MACHINE

[75] Inventor: Russell Olesen, Huntington, N.Y.

[73] Assignee: Puritan-Bennett Corporation, Kansas City, Mo.

[21] Appl. No.: 267,348

[22] Filed: May 26, 1981

[51] Int. Cl.³ ............................................. F16K 17/06
[52] U.S. Cl. ................................. 137/514.5; 137/469; 137/540
[58] Field of Search ................... 137/514.5, 540, 469, 137/475, 476, 477, 478

[56] References Cited

U.S. PATENT DOCUMENTS

| | | | |
|---|---|---|---|
| 1,252,940 | 1/1918 | Osborne | 137/514.5 |
| 2,628,633 | 2/1953 | Folmsbee | 137/469 |
| 2,792,015 | 5/1957 | Smith | 137/469 |
| 2,940,472 | 6/1960 | Chilcoat | 137/540 |
| 3,393,702 | 7/1968 | Ferrill | 137/478 X |
| 3,406,712 | 10/1968 | Weise | 137/477 X |

FOREIGN PATENT DOCUMENTS 56-42771  4/1981  Japan ................................. 137/469

*Primary Examiner*—Robert G. Nilson
*Attorney, Agent, or Firm*—Fulwider, Patton, Rieber, Lee & Utecht

[57] ABSTRACT

A pop-off valve (92) having a significantly improved pressure-flow characteristic and resistance to vibration or "honking." The valve includes a poppet (154) having a flat bottom end wall exposed to pressure and a peripheral lip with a frusto-conical surface (158) for engagement with a valve seat 140. A vent-hole (196) in the poppet further enhances the vibration characteristics of the valve, and a dampening chamber (186) downstream of the poppet dampens any remaining vibrations.

6 Claims, 8 Drawing Figures

POP-OFF GAS EVACUATOR VALVE FOR ANESTHESIA MACHINE

BACKGROUND OF THE INVENTION

This invention relates generally to anesthesia machines, and, more particularly, to pressure relief valves, usually referred to as pop-off valves, for the evacuation of excess gas from a patient breathing system used in conjunction with a gas anesthesia machine. In a gas anesthesia machine, an anesthetic gas, such as nitrous oxide ($N_2O$), is mixed with oxygen and, in some applications, passed through a vaporizer before emerging at a common outlet from the machine.

The common outlet is connectable directly to a patient breathing system, which is typically a closed system in which a patient undergoing anesthesia breathes in both recirculated gas, and gas supplied from the common outlet. Recirculated gas is obtained by processing exhaled gas through a carbon dioxide absorber and merging this flow with that from the common outlet. Check valves in the breathing system prevent the patient from exhaling directly back toward the common outlet, and from inhaling from the inlet side of the carbon dioxide absorber. Also included in the circle breathing system is a breathing bag, which fills with gas when the patient exhales and empties again when the patient inhales, some of the gas in the bag being recirculated through the carbon dioxide absorber and back to the patient.

Alternatively, if the patient is incapable of breathing, the breathing bag may be replaced by a gas-driven ventilator bellows, which fills during exhalation of gas from the patient's lungs and is emptied when drive gas is applied to the outside of the bellows during an inhalation phase of the breathing cycle. Application of the drive gas is controlled in response to sensed pressure, flow rate, or both, in the tube through which the patient breathes.

In one sense, the patient breathing system is a closed system, since some of the gas exhaled by the patient is processed by the absorber and recycled to the patient. However, since fresh anesthesia gas and oxygen may be continually supplied through the common outlet, the system is not a completely closed one, and some means must be provided to evacuate excess gas from the breathing system, to compensate for the gas drawn from the common outlet. Regardless of whether the breathing bag or the ventilator is used, a relief valve is provided to vent the excess gas at some stage during each breathing cycle. The relief valve used in conjunction with the breathing bag is referred to as a pop-off valve, and it is with this valve that the present invention is concerned. The vented gas is not allowed to escape directly to atmosphere, but is passed through an evacuator interface unit to a vacuum line. However, the gas evacuator interface forms no part of the present invention.

The pop-off valve typically comprises a relatively lightweight valve closure element which is spring biased against a valve seat. When a predetermined pressure is applied beneath the valve closure, it is lifted from the seat and gas is vented through an outlet port. The pressure threshold at which the valve opens is adjustable by varying the biasing force on the valve, and may be as low as a few centimeters of water to 10 or more centimeters of water. The valve has to be able to handle flow rates up to approximately 15 liters per minute, and ideally the valve opening pressure should not increase unduly as the flow rate increases.

In the past, pop-off valves have been subject to a number of significant disadvantages. First, pop-off valves have been subject to a vibration condition known as "honking," wherein the valve closure oscillates with respect to the valve seat. The resultant vibration is transmitted throughout the breathing system, and can induce vibration in other valves in the system. Dampening chambers on the downstream side of the pop-off valve have been used to minimize transmission of "honking" noise, but have not been completely successful. In addition, some prior art valves have not been able to operate at extremely low threshold pressures, below a few centimeters of water, and have a pressure-flow characteristic wherein the threshold pressure increases substantially as the flow rate is increased.

Accordingly, there has been a significant need for a pop-off valve that overcomes these disadvantages of prior art valves. The present invention satisfies this need.

SUMMARY OF THE INVENTION

The present invention resides in an improved pop-off valve for use in a gas anesthesia machine. The improved valve of the invention has a valve poppet in the form of a cylinder open at the top and closed at the bottom by a flat end wall which is presented toward the high-pressure side of the valve. A peripheral lip around the end wall has an interior conical surface sized to engage a seal on a valve seat.

The valve of the invention also includes a valve body in which the poppet is movable, a valve seat secured into the body, and fluid outlet means including a dampening chamber and an annular chamber connecting the dampening chamber with the interior of the valve body. Contributing to the improved characteristics of the valve are the shape of the valve poppet, to be contrasted with a generally hemispherical closure of the prior art, a vent passage extending through the sidewall of the cylindrical valve poppet into the annular chamber, to help minimize honking.

A coil spring is engageable with the upper face of the poppet end wall, and is secured to an axially movable plunger. When the plunger is withdrawn to a maximum-open condition, the spring does not bear on the valve poppet, which is then seated only under its own weight, providing for an extremely low opening pressure of approximately 0.6 cm of water.

The valve of the invention not only has a low minimum of opening pressure, but has a significantly flatter pressure-flow characteristic, i.e. its opening pressure increases only very slowly with increasing flow rate. Even more importantly, the improved valve of the invention is not subject to honking in the normal range of pressures and flows used in a practical application, but only at pressures above about 30 cm of water.

Accordingly, it will be appreciated that the valve of the present invention provides significant advantages over prior art valves, including reduction of honking and improved pressure-flow characteristics. Other aspects and advantages of this invention will become apparent from the following more detailed description, taken in conjunction with the accompanying drawings.

DESCRIPTION OF THE PREFERRED EMBODIMENT

Figure 2:
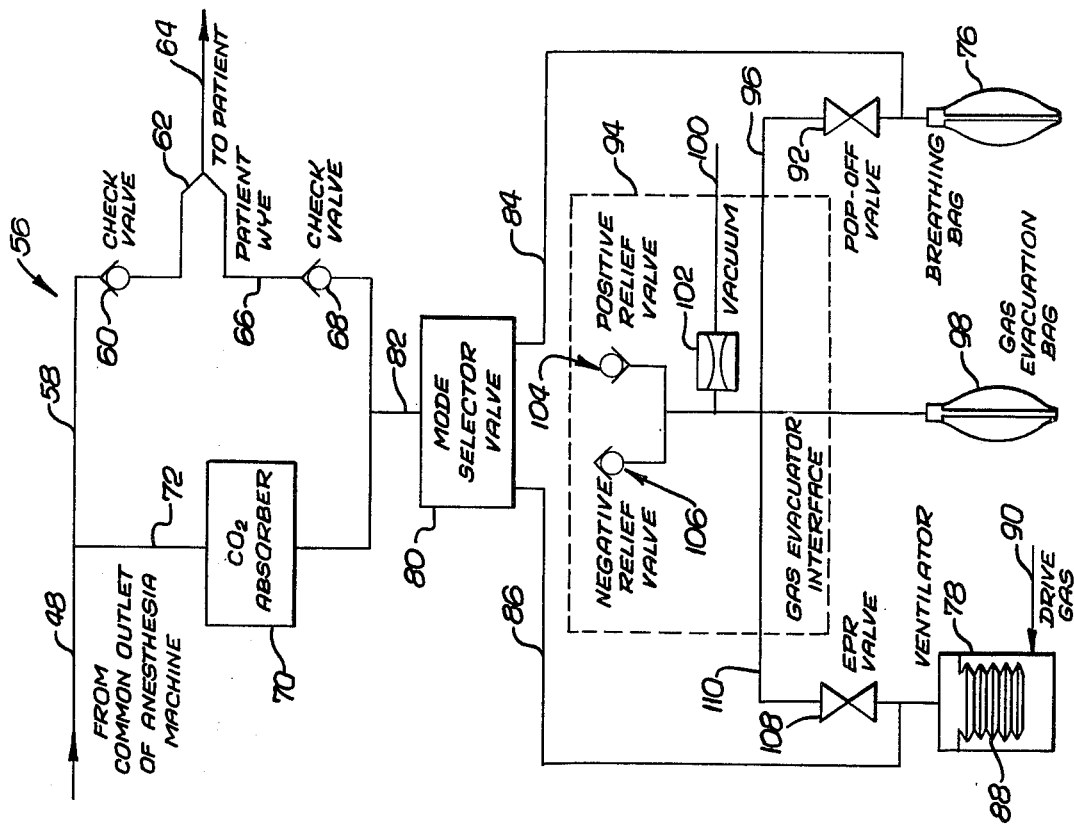
FIG. 2 is a simplified schematic flow diagram of a patient breathing system and gas evacuation system for use with a gas anesthesia machine.

As shown in the drawings for purposes of illustration, the present invention is principally concerned with a gas evacuator pop-off valve used in conjunction with a gas anesthesia machine to remove excess gas from a patient breathing system. Since the invention forms a small but significant part of a gas anesthesia system, the fundamentals of such a system will first be described by way of background.

Figure 1:
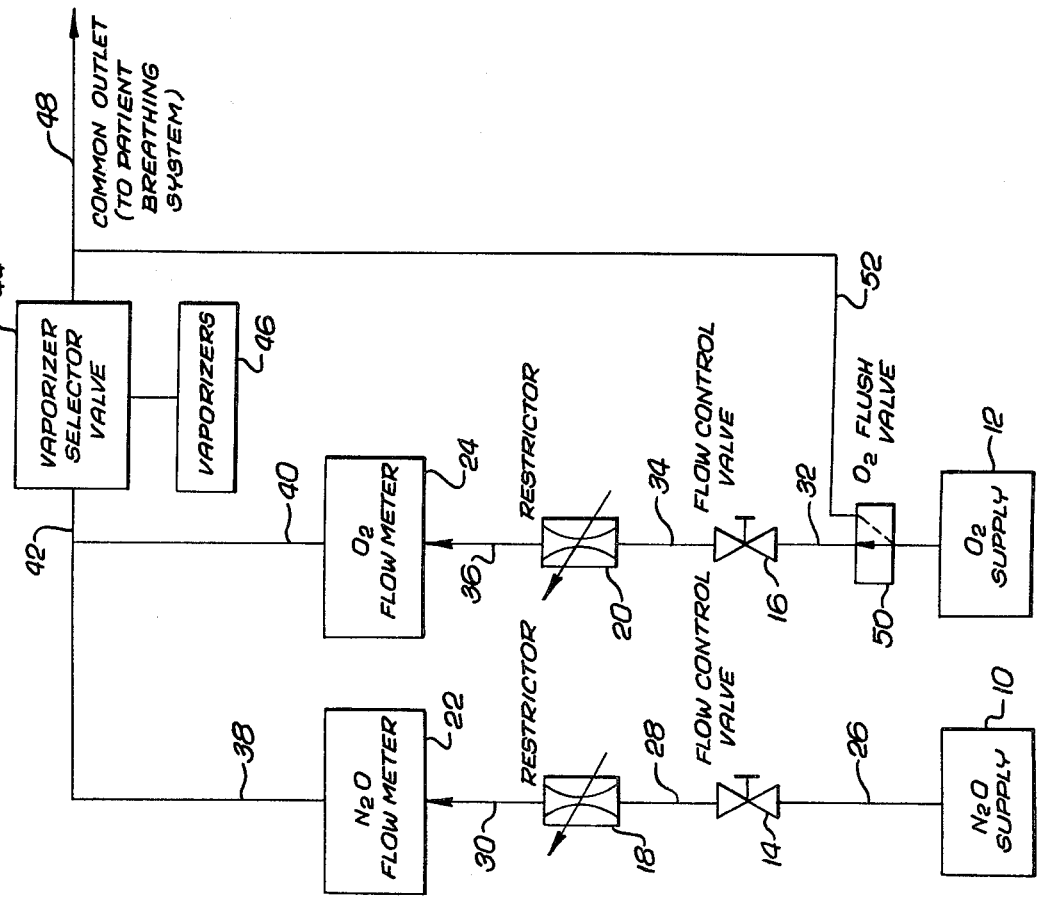
FIG. 1 is a simplified schematic flow diagram of a typical gas anesthesia machine.
Figure 3:
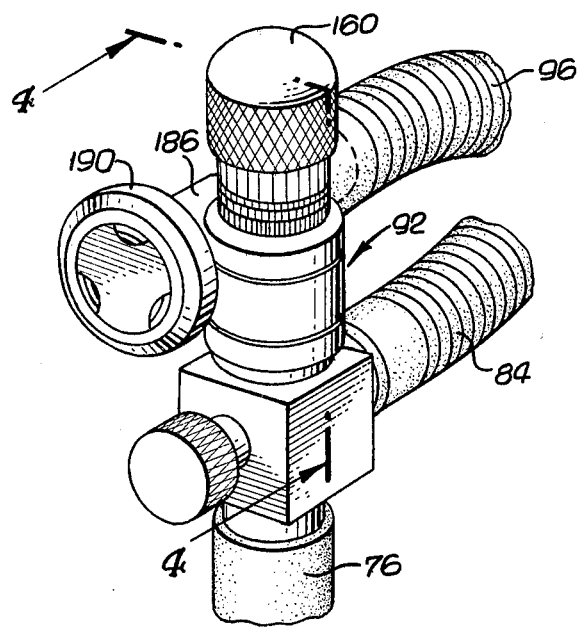
FIG. 3 is a perspective view of the pop-off valve of the invention.
Figure 4:
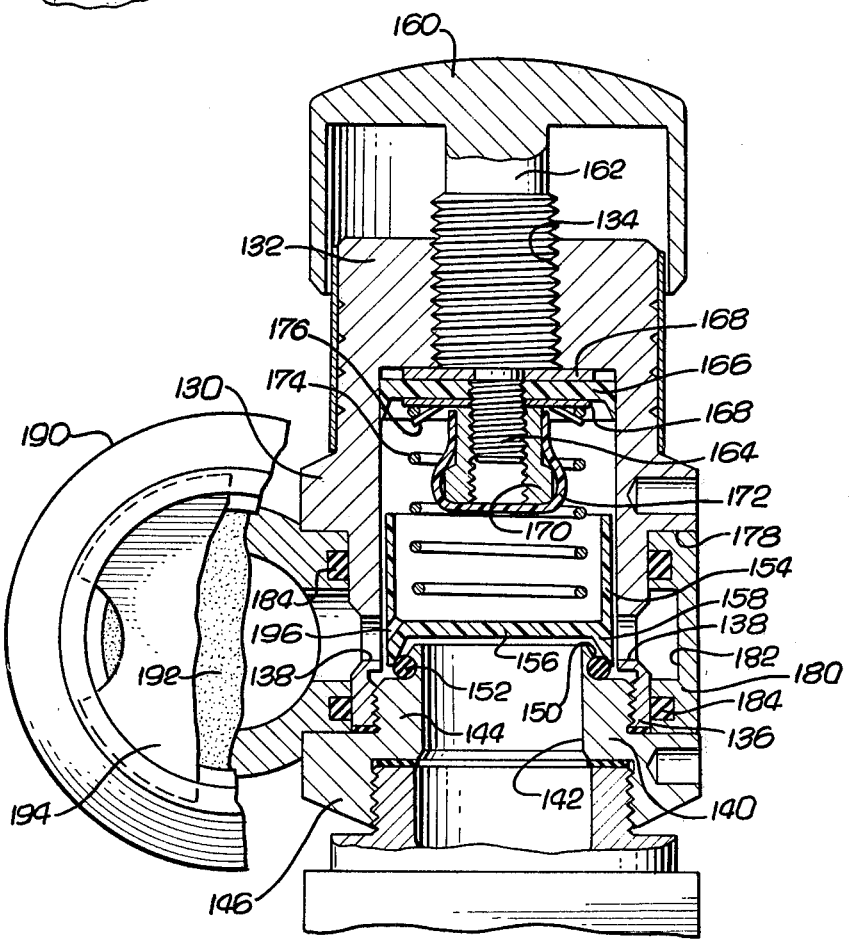
FIG. 4 is an enlarged sectional view of the pop-off valve, taken substantially along the line 4—4 in FIG. 3, and showing the valve closure minimally biased against its seat.

As shown in the simplified schematic flow diagram of FIG. 1, a gas anesthesia machine is basically a device for controlling the flow of anesthesia gas, such as nitrous oxide ($N_2O$), and oxygen ($O_2$) to a patient undergoing surgical treatment. Accordingly, the anesthesia machine includes a nitrous oxide supply, indicated by reference numeral 10, an oxygen supply 12, two flow control valves 14 and 16 for the nitrous oxide and oxygen, respectively, two variable restrictors 18 and 20, two flow meters 22 and 24, and interconnecting flow lines to be described more specifically. The nitrous oxide supply 10 is connected by line 26 to its flow control valve 14 and then by line 28 to the flow restrictor 18. Line 30 connects the restrictor 18 to the flow meter 22. Similarly, the oxygen supply 12 is connected by line 32 to the flow control valve 16, and thence by supply line 34 to the variable restrictor 20. Line 36 connects the restrictor 20 to the oxygen flow meter 24.

From the flow meters 22 and 24 lines 38, and 40 combine into a single manifold 42, which is connected to vaporizer selector valves, indicated at 44. The valves 44 may optionally select a vaporizer, indicated at 46, through which the gas is passed before proceeding to a common outlet 48. Typically, there is also an oxygen flush valve 50 connected in the line 32 from the oxygen supply to the oxygen flow valve 16. The flush valve 50 normally connects the oxygen supply 12 to the flow valve 16, but is operable to switch the oxygen supply directly to another flow line 52, connected directly to the common outlet 48 and bypassing the oxygen flow control valve 16, restrictor 20 and flow meter 24, as well as the vaporizer selector valves 44. The oxygen flush valve 50 is used in situations where an immediate flow of oxygen is required to the common outlet to flush any anesthesia gas that might still remain there.

As shown in FIG. 2, gas from the common outlet 48 is introduced into a patient breathing system, indicated generally by reference numeral 56. Gas from the common outlet 48 is received over an inhalation line 58, which passes through a first check valve 60 and thence to a patient wye 62, to which is connected a breathing tube 64 or a mouthpiece (not shown) through which the patient breathes. The patient wye 62 connects the patient breathing tube 64 to the inhalation line 58 and to an exhalation line 66. The exhalation line 66 includes a second check valve 68 and is connected to a carbon dioxide ($CO_2$) absorber 70, and thence by a line 72 back to the inhalation line 58. The check valve 60 in the inhalation line 48 operates to ensure that no exhalation gas from the patient passes along the inhalation line, and the other check valve 68 performs a corresponding function in the exhalation line 66, ensuring that gas is not inhaled through the exhalation line.

When the patient exhales, an expandable volume must be provided in the breathing system for the exhaled gas. If the patient is breathing spontaneously, this excess volume is usually provided in the form of an expandable breathing bag 76. Alternatively, if the patient is incapable of spontaneous breathing a ventilator 78 is typically employed both to receive exhaled gas from the patient and to pump inhalation gas back to the patient. These two modes of operation, i.e. breathing bag and ventilator modes may be selected by a mode selector valve 80 connected by line 82 to the exhalation line 66. The mode selector valve is basically a two-way pneumatic valve by means of which the line 82 is connected either to line 84 to the breathing bag 76 or to line 86 to the ventilator 78. First, with respect to breathing bag operation, when the patient exhales, gas passes through the check valve 68, the mode selector valve 80 and over line 84 to the breathing bag 76. When the patient inhales, the check valve 68 prevents the same gas from being drawn back to the patient over the exhalation line 66. Instead, gas is drawn from the breathing bag 76 back along the line 84, through the mode selector valve 80, through the $CO_2$ absorber 70, and back to the inhalation line 58. If the patient has difficulty inhaling, an anesthesiologist may provide assistance by squeezing the breathing bag 76 during each inhalation phase, although if the patient has difficulties over a prolonged period, the ventilator mode of operation would normally be selected.

In the ventilator mode, exhaled gas from the patient passes through the check valve 68 and over line 82 to the mode selector valve 80. From there gas passes over line 86 to the ventilator 78, which includes a bellows 88. The line 86 is connected directly to a chamber formed inside the bellows 88, so that exhaled gas expands the bellows in the same way that the breathing bag was expanded in the breathing bag mode of operation. At the end of the exhalation phase of the breathing cycle, a drive gas is applied to the outside of the bellows 88, as indicated by the arrow 90. The drive gas collapses the bellows 88 and drives the gas contained in it back along the line 86, through mode selector valve 80 and into the absorber 70, from which gas may be returned to the patient inhalation line 58.

In both the breathing bag mode and the ventilator mode, the breathing system is a closed system, in the sense that the patient may breathe recirculated gas, after it has been processed through the $CO_2$ absorber. It is an open system, however, in the sense that additional anesthesia gas and oxygen may be supplied through the common outlet 48. Accordingly, some means must be provided for evacuating excess gas from the patient breathing system to compensate for the gas added from the common outlet 48. For breathing bag operation, the excess gas is vented through a pop-off valve 92 connected to the breathing bag 76 and to line 84. The pop-off valve 92 is a positive relief valve operable during the exhalation phase of a spontaneous breathing cycle to evacuate excess gas from the breathing system. However, the pop-off valve 92 cannot be allowed to vent the excess gas directly to atmosphere because this would expose personnel in the operating room to significant concentrations of anesthesia gas. Nor can the pop-off valve 92 be connected directly to a vacuum or waste line, because this would expose the patient to undesirable vacuum pressures. A solution is found in a gas evacuator interface, indicated by reference numeral 94.

The pop-off valve 92 is connected by line 96 to the interface 94, and is connected in fluid communication with a gas evacuation bag 98, in which the evacuated gas is temporarily stored. A vacuum line 100 is also connected to the interface 94, through a flow restrictor 102, and the vacuum draws gas from the gas evacuation bag 98 at a relatively constant rate. In normal operation, gas is evacuated periodically through the pop-off valve 92, during a portion of each exhalation phase, and is stored temporarily in the gas evacuation bag 98. The vacuum line 100 withdraws the gas from the bag 98, and the system attains a working equilibrium without applying any excess of positive or negative pressure to the patient breathing system 56. For use in the event that the vacuum does not withdraw enough gas from the gas evacuation bag 98, a positive relief valve 104 is provided in the interface 94, to ensure that excessive positive pressure is not applied to the patient breathing system 56. Similarly, if the vacuum line 100 applies excessive suction to the interface 94, a negative relief valve 106 operates to vent the system and allow the vacuum line 100 to draw atmospheric air rather than applying excessively negative pressure to the patient breathing system 56.

To serve a similar function to the pop-off valve 92 there is an expiratory pressure relief (EPR) valve 108 connected to the line 86 from the ventilator bellows 88. The EPR valve 108 is held in a closed condition whenever drive gas is applied over line 90, but is permitted to open during the exhalation phase, when the drive gas pressure is lowered and a preselected positive pressure is attained in line 86 from the patient breathing system. Vented gas in line 86 passes over line 110 to the gas evacuator interface 94, and is treated in the same manner as gas over line 96 from the pop-off valve 92.

It is highly desirable to have a pop-off valve that opens positively at a selected threshold pressure, the opening pressure being relatively insensitive to flow rates over a typical operating range up to 15 liters per minute. In valves available heretofore, a valve poppet could be lifted subject to back pressure from above once the poppet had lifted. Flow around the poppet could apply sufficient back pressure to close the valve again, and an undesirable resonation could occur. This phenomenon, commonly referred to as "honking," occurred over a wide range of valve opening pressures and flows, as indicated by the shaded region 120 in FIG. 7. It will be noted that the honking region 120 overlaps the typical operating region 122.

Figure 7:
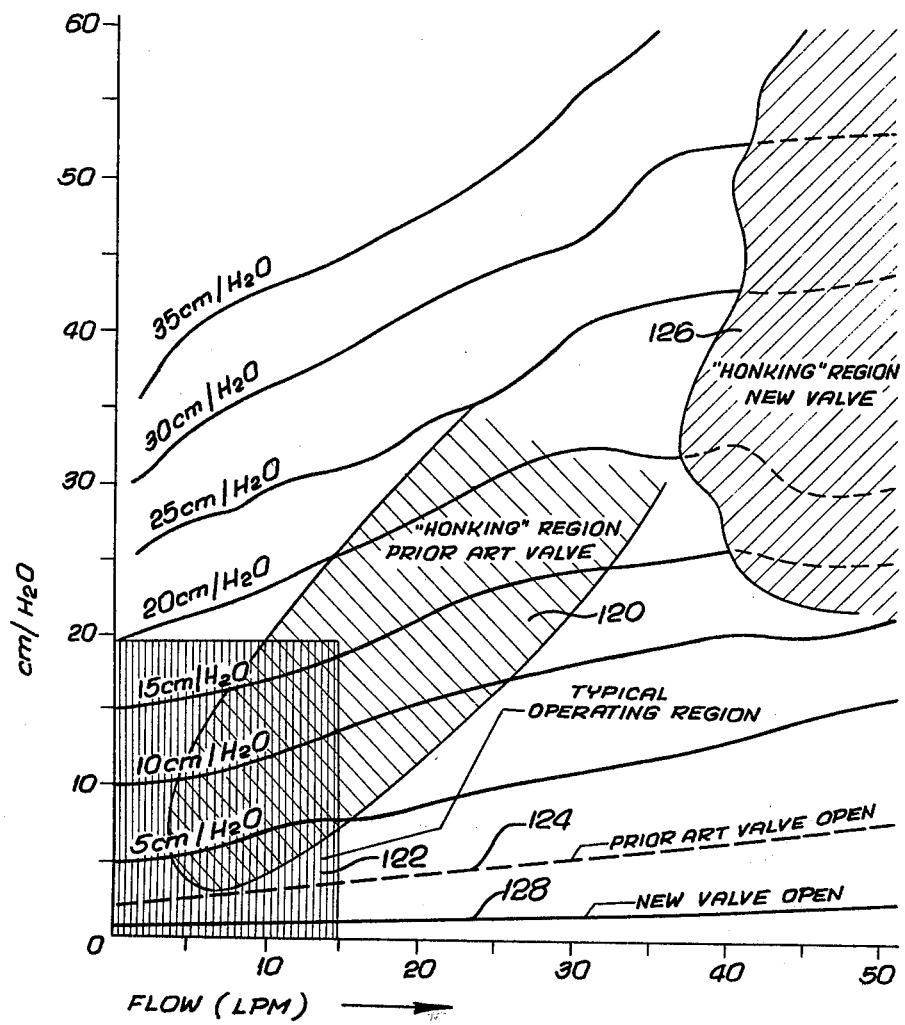
FIG. 7 is a graphical representation of the pressure-versus-flow characteristic of the valve.

As also shown in FIG. 7, at curve 124, a typical prior art valve has an opening pressure that increases significantly with flow rate. Moreover, the minimum opening pressure obtainable is approximately 2-3 cm water.

Figure 8:
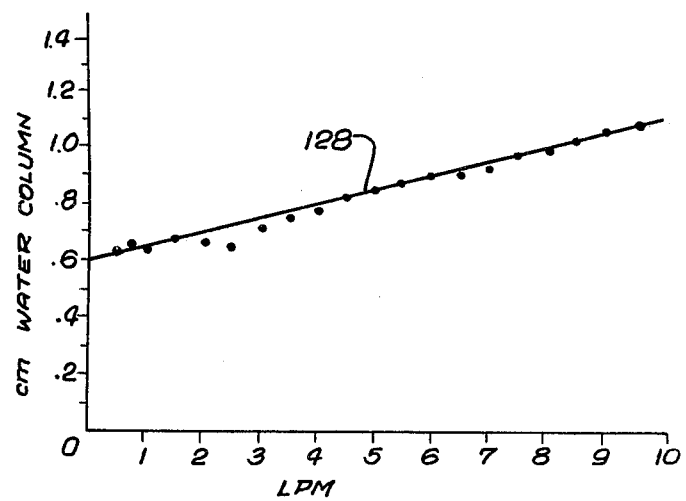
FIG. 8 is an enlarged-scale graph showing pressure-versus-flow in a fully open valve condition, i.e. with the valve not biased.

In accordance with the invention, a pop-off valve 92 is configured to move the honking region, indicated at 126 (FIG. 7), far from the typical operating region 122. In addition, the new valve 92 has a pressure-flow characteristic in which the opening pressure does not increase with flow as steeply as prior art valves. For example, the characteristic of the new valve when not spring-biased at all is shown at 128 in FIG. 7. It will be observed from this curve 128, and the enlarged form of it in FIG. 8, that the minimum valve opening pressure is at or below 1.0 cm of water over the flow range 0–10 liters per minute, comparing favorably with the 2-3 cm of water associated with prior art valves.

More specifically, and as shown in FIGS. 3-6, the valve 92 of the invention includes a generally cylindrical housing 130 having an upper end portion 132 that is closed except for a threaded axial hole 134 therethrough, and an open bottom end portion 136 with a female threaded area and a plurality of radial openings 138 through the sidewall of the housing. A valve seat 140 is secured to the bottom end portion 136 of the housing 130. The seat 140 has a central bore 142, a threaded shank 144 for engaging the housing 130 and a flanged portion 146 somewhat larger in diameter than the housing. A gasket 148 provides a seal between the housing 130 and the seat flanged portion 146. The valve seat 140 presents a frusto-conical surface 150 toward the top end portion 132 of the housing, the surface being annularly recessed to accomodate an O-ring seal 152.

A lightweight valve poppet 154 is dimensioned for a loose fit inside the housing 130 and is cylindrical in shape, open at its top end and having a flat lower end wall 156 and an integral annular lip 158 around the periphery of the end wall. The lip 158 presents a cylindrical surface outwardly toward the housing 130 and a frusto-conical surface inwardly, for self-centering engagement with the O-ring seal 152.

An adjustment knob 160 has a threaded shank 162 that engages the hole 134 in the top of the housing 130. At the end of the shank 162 is a reduced-diameter portion 164, also threaded, on which is mounted a seal 166 engaging the inner sidewall of the housing 130 and sandwiched by washers 168. A nut 170 secures the seal 166 and washers 168 to the shank portion 164, and a plastic sleeve 172 covers the nut.

Figure 6:
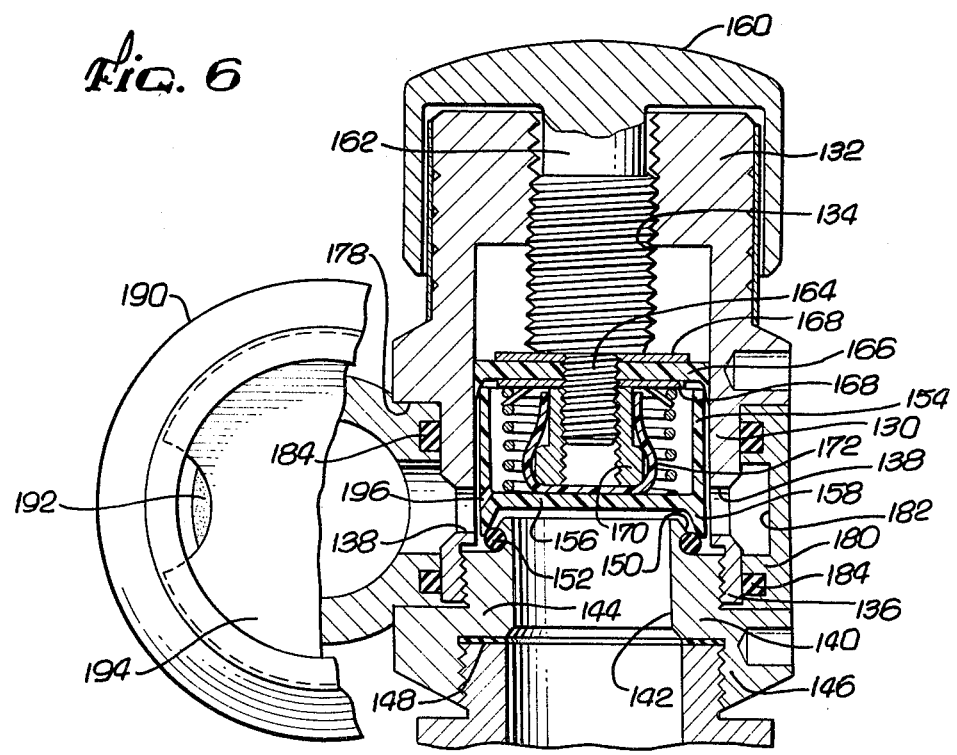
FIG. 6 is another sectional view similar to FIG. 4, but showing the valve closure maximally biased against its seat.

Surrounding the nut 170 is a coil spring 174, retained in contact with the lower seal washer 168 by a retaining lip 176 on the washer, and extending down into the poppet 154. When the knob 160 is rotated in towards the housing 130, the spring 174 is compressed and the poppet 154 is biased onto the O-ring 152 in the valve seat 140, as shown in FIG. 6. When the knob is rotated to its fullest extent in the opposite direction, the spring biasing force is removed from the poppet 154, which is held in a sealing relationship with the valve seat 140 only by its own weight.

The valve housing 130 also has an annular shoulder 178 about midway along its outer wall, the shoulder and the flange 146 together forming an annular recess to accommodate a collector ring 180. The collector ring 180 has an internal annular recess 182 to provide fluid communication with the radial holes 138 in the valve housing 130, and has two seals 184 to seal the ring to the housing. On one side of the ring, there is a cylindrical dampening chamber 186 with which the recess 182 is in fluid communication. The chamber 186 is oriented perpendicularly with respect to the housing 130, and provides an outlet path from the valve 92 to line 96.

Figure 5:
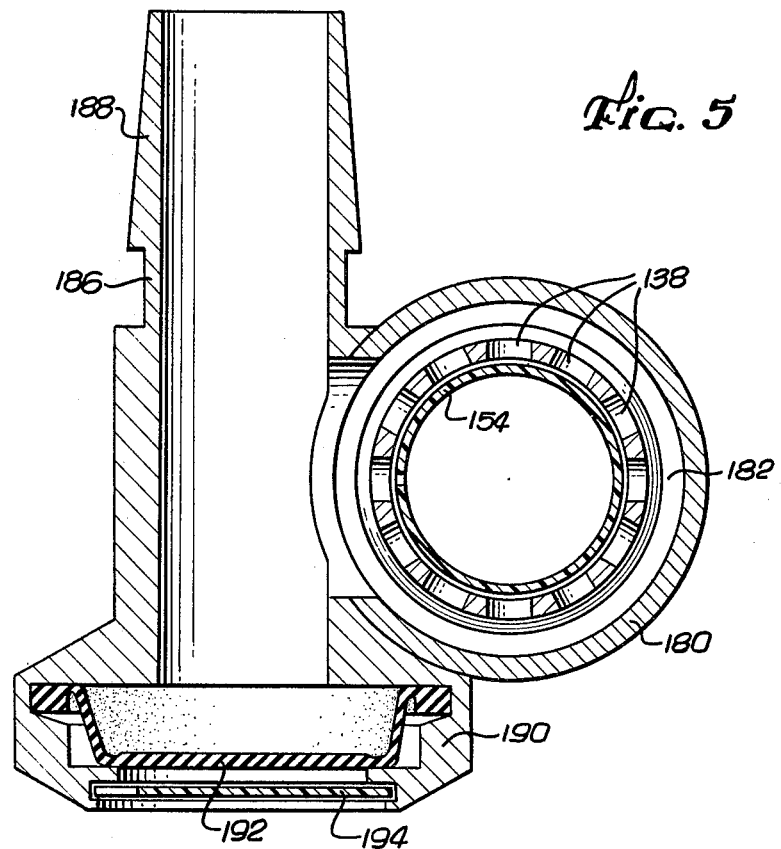
FIG. 5 is another sectional view of the pop-off valve, taken substantially along the line 5—5 in FIG. 4.

As best shown in FIG. 5, the dampening chamber includes a nipple end 188 for attachment to a hose, and a closed end 190, having a resilient closure 192 and protective cover 194. The dead space provided at the closed end 190 of the chamber facilitates dampening of vibration and is a contributing factor to the favorable honking characteristic of the valve.

Another factor contributing to the desirable characteristics of the valve is a vent-hole 196 extending through the sidewall of the valve poppet 154, from inside the poppet to an outside region adjacent to the radial holes 138 in the housing 130. The vent-hole 196 allows gas to bleed through the poppet 154 in much the same way as a bleed hole in a shock absorber. Its effect, together with that of the flat poppet undersurface, is to help shift the point of resonance or honking of the valve away from the normal operating region.

It will be appreciated from the foregoing that the present invention represents a significant advance in the field of pop-off relief valves for use in gas anesthesia machines. In particular, the invention provides a valve having a significantly superior pressure-flow characteristic, and having, for all practical purposes, no honking problem at all. It will also be appreciated that, although a specific embodiment of the invention has been described in detail for purposes of illustration, various modifications may be made without departing from the spirit or scope of the invention. Accordingly, the invention is not to be limited except as by the appended claims.

I claim:

1. A pop-off valve for use in a gas anesthesia machine, said valve comprising:
   a valve housing having a lower end and a closed upper end;
   a valve seat located in said lower end and being connectable to a breathing system from which excess pressure is to be relieved;
   a valve poppet sized to slide freely in said body and having a cylindrical shape with a closed lower end wall and a peripheral wall about said end presenting a frustoconical surface to said valve seat;
   a compression spring for biasing said valve poppet onto said valve seat;
   means for adjusting the spring-biasing force applied to said valve poppet;
   a plurality of openings in said housing close to said valve seat, to provide a fluid path for gas after said valve poppet is lifted from said valve seat; and
   fluid communication means for connecting said plurality of openings with an output line;
   whereby the shape of said poppet provides an improved valve characteristic and effectively eliminates valve vibration, and wherein said valve poppet includes at least one vent-hole extending through its sidewall, to provide a controlled dampening effect on rapid movements of said valve poppet, thereby further moving a resonance condition away from a normal operating region.

2. A pop-off valve for use in a gas anesthesia machine, said valve comprising:
   a valve housing having a lower end and a closed upper end;
   a valve seat located in said lower end and being connectable to a breathing system from which excess pressure is to be relieved;
   a valve poppet sized to slide freely in said body and having a cylindrical shape with a closed lower end wall and a peripheral wall about said end presenting a frusto-conical surface to said valve seat;
   a compression spring for biasing said valve poppet onto said valve seat;
   means for adjusting the spring-biasing force applied to said valve poppet;
   a plurality of openings in said housing close to said valve seat, to provide a fluid path for gas after said valve poppet is lifted from said valve seat; and
   fluid communication means for connecting said plurality of openings with an output line, said fluid communications means including a dampening chamber to absorb any vibrations of said valve poppet and inhibit their transmissions away from said valve;
   whereby the shape of said poppet provides an improved valve characteristic and effectively eliminates valve vibration, and wherein said valve poppet includes at least one vent-hole extending through its sidewall, to provide a controlled dampening effect on rapid movements of said valve poppet, thereby further moving a resonance condition away from a normal operating region.

3. A pop-off valve as set forth in claim 2, wherein said valve seat includes an O-ring seal with which said frusto-conical surface on said valve poppet engages.

4. A pop-off valve for use in a gas anesthesia machine, said valve comprising:
   a valve housing having a lower end and a closed upper end;
   a valve seat located in said lower end and being connectable to a breathing system from which excess pressure is to be relieved;
   a valve poppet sized to slide freely in said body and having a cylindrical shape with a closed lower end wall and a peripheral wall about said end presenting a frusto-conical surface to said valve seat;
   a compression spring for biasing said valve poppet onto said valve seat;
   means for adjusting the spring-biasing force applied to said valve poppet, said means including an adjustment knob having a shaft threadably coupling to said closed end of said housing and extending therethrough, and spring retaining means for securing said compression spring to said shaft within said housing, whereby rotation of said knob varies the compressive force applied to said valve poppet by said spring;
   a plurality of openings in said housing close to said valve seat, to provide a fluid path for gas after said valve poppet is lifted from said valve seat; and
   fluid communication means for connecting said plurality of openings with an output line;
   whereby the shape of said poppet provides an improved valve characteristic and effectively eliminates valve vibration.

5. A pop-off valve as set forth in claim 4, wherein said adjustment means places no biasing force on said valve poppet when said shaft is withdrawn to the greatest extent, and the valve poppet is seated only under its own weight.

6. A pop-off valve as set forth in claim 4, wherein the end of said shaft is encased in a soft material, to minimize damage to said valve poppet when said shaft is rotated into said valve housing to its greatest extent, and said poppet is held closed against said seat by said shaft.

* * * * *